(12) United States Patent
Llaguno et al.

(10) Patent No.: US 12,117,432 B2
(45) Date of Patent: Oct. 15, 2024

(54) SYSTEM AND METHOD FOR ANALYSIS OF A FLUID

(71) Applicant: S.C.R. (Engineers) Limited, Netanya (IL)

(72) Inventors: Ana Carmen Alatorre Llaguno, Hamilton (NZ); Robert Graham Orchard, Hamilton (NZ)

(73) Assignee: S.C.R. (Engineers) Limited, Netanya (IL)

( * ) Notice: Subject to any disclaimer, the term of this patent is extended or adjusted under 35 U.S.C. 154(b) by 0 days.

(21) Appl. No.: 18/131,685

(22) Filed: Apr. 6, 2023

(65) Prior Publication Data

US 2023/0243799 A1 Aug. 3, 2023

Related U.S. Application Data

(63) Continuation of application No. 16/761,678, filed as application No. PCT/NZ2018/050153 on Oct. 31, 2018, now Pat. No. 11,644,453.

(30) Foreign Application Priority Data

Nov. 7, 2017 (NZ) ........................................ 737052

(51) Int. Cl.
  *G01N 33/04* (2006.01)
  *G01N 11/02* (2006.01)
  *G01N 11/00* (2006.01)

(52) U.S. Cl.
  CPC ............. *G01N 33/04* (2013.01); *G01N 11/02* (2013.01); *G01N 2011/006* (2013.01)

(58) Field of Classification Search
  CPC .. G01N 33/04; G01N 11/02; G01N 2011/006; G01N 33/06; G01N 33/0006; G01D 18/00

(Continued)

(56) References Cited

U.S. PATENT DOCUMENTS 5,137,738 A 8/1992 Wynn
5,583,282 A 12/1996 Tom
(Continued)

FOREIGN PATENT DOCUMENTS

CN 1570627 1/2005
CN 103149278 6/2013
(Continued)

OTHER PUBLICATIONS

Milkotester, "Master milk analyser by Milkotester Ltd (www.milkotester.com); online at: https://milkotester.com/collections/our-products/products/master-pro-touch; Sep. 21, 2017".

(Continued)

*Primary Examiner* — Robert R Raevis
(74) *Attorney, Agent, or Firm* — GableGotwals

(57) ABSTRACT

A system for analysing a fluid is described, including an in-line sensor configured to analyse a fluid flowing past the in-line sensor to determine at least one in-line value of a fluid parameter of the fluid across an event period, and a sample sensor configured to analyse a sample of fluid extracted from the flow of fluid during the event period, to determine a sample value of the fluid parameter for the sample. At least one processor is provided, configured to determine a representative in-line value of the fluid parameter across the event period based at least in part on the at least one in-line value, and determine an overall representative value of the fluid parameter across the event period based on the representative in-line value, the sample value for the sample, and one or more of the in-line values corresponding to the time of extracting the sample, wherein determination of the overall representative value is based on an error correction value determined for the in-line sensor during the event period.

20 Claims, 9 Drawing Sheets

(58) Field of Classification Search
USPC ............ 73/1.02, 23.21, 61.41–61.61,
73/61.71–61.75; 324/425–450, 601, 130;
356/432, 444; 702/85, 104;
422/82.01–82.11, 83, 98
See application file for complete search history.

(56) References Cited

U.S. PATENT DOCUMENTS

2010/0047848 A1  2/2010  Law et al.
2017/0102370 A1  4/2017  Alber et al.

FOREIGN PATENT DOCUMENTS

| | | |
|---|---|---|
| CN | 103528877 | 1/2014 |
| EP | 3045891 A1 | 7/2016 |
| GB | 2472503 B | 7/2013 |
| WO | 9820338 A1 | 5/1998 |
| WO | 0042427 A1 | 7/2000 |
| WO | 02100164 A1 | 12/2002 |
| WO | 2011091805 A1 | 8/2011 |
| WO | 2014179065 A1 | 11/2014 |

OTHER PUBLICATIONS

Lactoscan, "Milk Analyser by Milkotronic Ltd.; online at: https://www.milkotronic.com/; Sep. 4, 2017".
Miristm Dairy Milk Analyzer by Miris Holding ABH, "Online at: https://www.mirissolutions.com/our-products; May 2, 2006".

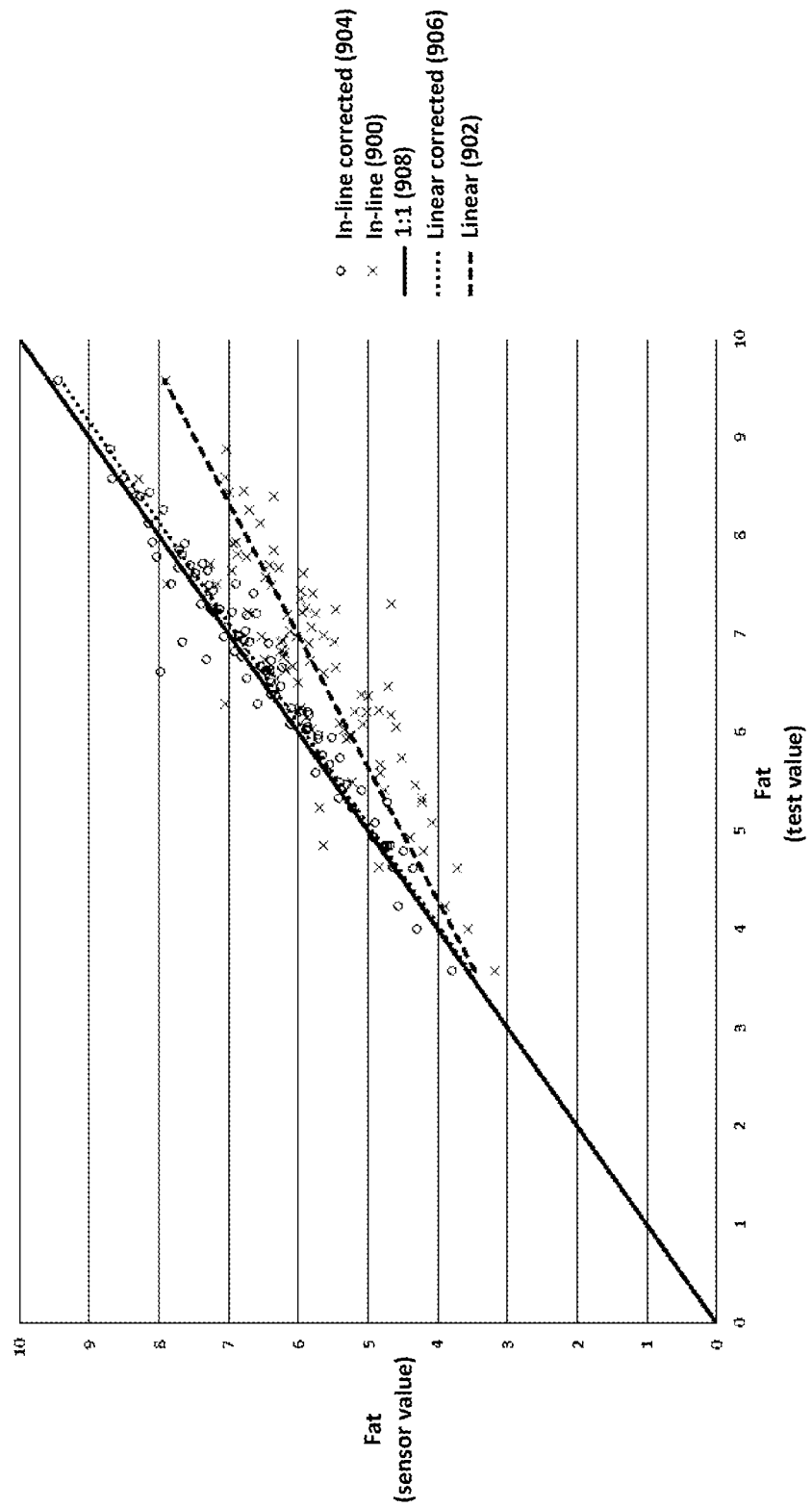

SYSTEM AND METHOD FOR ANALYSIS OF A FLUID

CROSS-REFERENCE TO RELATED APPLICATIONS

This is a continuation application of U.S. application Ser. No. 16/761,678 filed May 5, 2020 which claims priority PCT Application No. NZ2018/050153 filed 31 Oct. 2018 which claims priority to provisional New Zealand Patent Application No. 737052 filed 7 Nov. 2017, each of which are incorporated herein by reference.

BACKGROUND OF THE INVENTION

The present disclosure relates to a system and method for analysis of a fluid—more particularly for analysis of the fluid using an in-line sensing device in combination with a sample sensing device, and more particularly for analysis of milk.

The use of sensors to obtain information relating to milk collected from dairy animals is well known. Such information is used in decision making regarding such matters as processing of the milk, culling, breeding, medical treatment, animal specific feed rations as well as measurement of milk production efficiency.

Numerous portable off-line analysers are known in the art for analysing a sample of milk to determine parameters such as fat, protein, lactose and total solids. Examples of such analysers using ultrasound analysis include the Lacti-Check™ milk analyser by Page & Pedersen International, Ltd (www.pagepedersen.com); the Master milk analyser by Milkotester Ltd (www.milkotester.com); the LACTOSCAN™ milk analyser by Milkotronic Ltd (www.lactoscan.com). Other analytical techniques are also known, for example mid-infrared spectroscopy, as exemplified by the MIRIS™ Dairy Milk Analyzer by Miris Holding AB (www.mirissolutions.com).

Such off-line analysers are generally capable of relatively high precision measurements in comparison with commercially available in-line sensors—but have practical limitations associated with the requirement that the analysis be performed on a discrete sample. In particular, measurements from the sample may not be representative of the milk parameter across the entire milking. For example, the variability of fat content across the course of a milking is such that a spot sample is unlikely to be representative of the average fat value of milk collected.

In-line sensors are also known for use in the measurement of parameters of the milk flowing through them, without the requirement for a sample to be collected and delivered to them. As such, they are capable of collecting data across the entirety of the milking. However, in order to achieve an acceptable price-point, and to meet the constraints imposed by flowing milk, such in-line sensors are generally of lower precision than the off-line analysers performing ultrasound or mid-infrared spectroscopy analysis.

It is an object of the present invention to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Further aspects and advantages of the present invention will become apparent from the ensuing description which is given by way of example only.

BRIEF SUMMARY OF THE INVENTION

According to one aspect of the present disclosure, there is provided a system for analysing a fluid. The system includes an in-line sensor configured to analyse a fluid flowing past the in-line sensor to determine at least one in-line value of a fluid parameter of the fluid across an event period. The system includes a sample sensor configured to analyse a sample of fluid extracted from the flow of fluid during the event period, to determine a sample value of the fluid parameter for the sample. The system includes at least one processor configured to determine a representative in-line value of the fluid parameter across the event period based at least in part on the at least one in-line value. The at least one processor is further configured to determine an overall representative value of the fluid parameter across the event period based on the representative in-line value, the sample value for the sample, and one or more of the in-line values corresponding to the time of extracting the sample, wherein determination of the overall representative value is based on an error correction value determined for the in-line sensor during the event period.

According to one aspect of the present disclosure, there is provided a method for analysing a fluid. The method includes the step of analysing a fluid flowing past an in-line sensor to determine at least one in-line value of a fluid parameter of the fluid across an event period. The method further includes the step of analysing, with a sample sensor, a sample of fluid extracted from the flow of fluid during the event period, to determine a sample value of the fluid parameter for the sample. The method further includes the step of determining a representative in-line value of the fluid parameter across the event period, based at least in part on the at least one in-line value. The method further includes the step of determining an overall representative value of the fluid parameter based on the representative in-line value, the sample value for the sample, and one or more of the in-line values corresponding to the time of extracting the sample, wherein determination of the overall representative value is based on an error correction value determined for the in-line sensor during the event period.

According to one aspect of the present disclosure, there is provided a system for analysing a fluid. The system includes an in-line sensor configured to analyse a fluid flowing past the in-line sensor to determine at least one in-line value of a fluid parameter of the fluid across an event period. The system includes a sample sensor configured to analyse a sample of fluid extracted from the flow of fluid during the event period, to determine a sample value of the fluid parameter for the sample. The system includes at least one processor configured to determine a representative in-line value of the fluid parameter across the event period based at least in part on the at least one in-line value. The at least one processor is further configured to determine a corrected representative value of the fluid parameter based on the representative in-line value, the sample value for the sample, and one or more of the in-line values corresponding to the time of extracting the sample.

According to one aspect of the present disclosure, there is provided a method for analysing a fluid. The method includes the step of analysing a fluid flowing past an in-line sensor to determine at least one in-line value of a fluid parameter of the fluid across an event period. The method further includes the step of analysing, with a sample sensor, a sample of fluid extracted from the flow of fluid during the event period, to determine a sample value of the fluid parameter for the sample. The method further includes the step of determining a representative in-line value of the fluid parameter across the event period, based at least in part on the at least one in-line value. The method further includes the step of determining a corrected representative value of the fluid parameter based on the representative in-line value, the sample value for the sample, and one or more of the in-line values corresponding to the time of extracting the sample.

Various configurations of sensors, in terms of how the sensor is exposed to the fluid to be analysed, are known in the art. Terms such as "in-line", "on-line", "at-line", "near-line" and "off-line" are used in the art to distinguish between these configurations—however there is a degree of inconsistency in their usage. Reference will be made herein to "in-line", "on-line", "off-line", and "sample" sensors, which for clarity may be defined as follows.

Reference herein to an in-line sensor should be understood to mean a sensor analysing fluid flowing past one or more sensing means, to determine at least one parameter of the fluid at a particular point or period of time—i.e. without collection of a discrete sample from the flow.

Reference to an on-line sensor should be understood to mean a sensor which automatically extracts a sample of fluid from a fluid flow, and analyses the sample of fluid to determine at least one parameter of the sample. As used herein, the term "on-line" may encompass embodiments in which the sample is returned to the fluid flow, or discarded.

The terms "at-line" and "off-line" may be used in the art to distinguish between the environment in which the sensor is configured to operate. Both at-line and off-line sensors are configured to analyse a discrete sample of the fluid delivered to the sensor by an operator. At-line sensors (which may be referred to as "near-line" sensors) are generally intended to be located within the vicinity of the fluid flow—for example, within a milking facility—while off-line sensors are primarily intended for use in a more environmentally controlled environment—for example, in a laboratory. In practice, particularly for milking operations, analysis of a sample by an off-line sensor may necessitate transport of the sample from the sample source to a remote facility. As used herein, the term "off-line" should be understood to refer to a sensor configuration in which a sample is collected from the fluid, and delivered to the sensor by an operator rather than an automated system.

On-line and off-line sensors, as defined herein, may be distinguished from in-line sensors by the act of analysing a sample extracted from the fluid flow rather than analysing the flow itself. As such, on-line and off-line sensors may be referred to in the collective as "sample" sensors.

In exemplary embodiments, the fluid may be milk extracted from a milking animal. It is envisaged that the present disclosure may have particular application to the analysis of milk during the transfer of milk from the point of extraction to a storage vessel. Milking plants typically include individual milk transport conduits from the points of extraction (for example, using a milking cluster including teat cups), joining to a common transport line for delivery to the storage vessel. The provision of in-line sensors within the individual milk transport conduits is known in the art—allowing for the analysis of milk extracted from an individual animal as it flows through those individual milk transport conduits.

However, it is envisaged that exemplary embodiments of the present disclosure may have application to other fluid types—particularly where the fluid is transported via a conduit, and has a parameter which varies over an event period. Exemplary embodiments of the present disclosure may have particular application to instances in which there is potential for bias in an in-line sensor measurement to change between event periods.

Reference to an event period should be understood to mean a period of time associated with an event, during which it is desirable to distinguish the value of the fluid parameter of the flow of fluid from the value of the fluid parameter during another period of time—i.e. the flow of fluid includes a plurality of event periods associated with discrete events, and it is desirable to analyse the fluid for each event period. It is also contemplated that the event period may be a period of time over which the average value of the parameter is representative of the average value over a longer time period—i.e. the event period is a sub-period within the entirety of the fluid flow.

For example, in the context of milking, the event period may be the milking of an individual animal. This allows for data to be collected which relates to that particular animal.

Numerous such in-line sensors are known for use in relation to milking animals. Non-limiting examples may include: composition sensors that measure properties of milk produced by an animal such as fat, protein, lactose, solids—not fat, and/or water content; yield sensors that measure a volume and flow-rate of milk produced by an animal; and milk conductivity sensors to identify animals suffering from mastitis. By way of example, the in-line sensor may be the YieldSense™ volume, fat, and protein sensor by LIC Automation Limited (www.licautomation.co.nz), or the AfiLab™ fat, protein and lactose concentration sensor by Afimilk Ltd (www.afimilk.com).

It is envisaged that exemplary embodiments of the present application may have particular application to the determination of fat content in milk. However, it should be appreciated that this is not intended to be limiting to all exemplary embodiments, and it is contemplated that other parameters of milk may be determined—for example lactose and protein content—or parameters of fluids other than milk.

The fact that in-line milk sensors analyse the milk as it flows past them prevents the use of sample treatments that can improve measurement. For example, known ultrasound milk analysers control milk temperature precisely to achieve higher precision measurement. Known mid-infrared analysers also control milk temperature and require a measurement cell much narrower than typical conduits for milk flow in which in-line sensors are positioned. Other treatments—including elimination of air bubbles, addition of reagents, and homogenisation—can be used in sample sensors but not in-line sensors, and may improve measurement performance. Furthermore, sample sensors can be fabricated using materials and geometries that do not meet hygiene requirements for milking systems and therefore cannot be used for in-line sensors. These limitations of in-line sensors contribute to their relatively low precision.

In-line sensors for milk take instantaneous readings of characteristics such as electric conductivity and optical properties and apply models to determine a value for one or more milk parameters at the time at which the instantaneous readings were obtained. For completeness, it should be understood that reference to sensing optical properties of a fluid may include sensing of properties with a sensor using electromagnetic radiation which is not within the visible spectrum (i.e. the in-line sensor may be an electromagnetic radiation-based sensor). Typically, measurements by in-line sensors rely on milk characteristics that are dependent on multiple attributes of the milk being analysed. Some of these milk attributes are unknown to the sensor and cannot be corrected for, resulting in measurement error. Some of the milk attributes contributing to measurement error in typical in-line milk sensors are believed to be relatively constant throughout the course of a milking, resulting in a relatively constant error throughout the course of a milking compared to the variation in error between event periods (i.e. between milkings).

In an exemplary embodiment, the in-line sensor is configured to obtain a plurality of in-line values of the fluid parameter across the event period. It should be appreciated that reference to the in-line sensor determining a plurality of in-line values of the fluid parameter is intended to encompass embodiments in which a continuous measurement is obtained (and discrete in-line values corresponding to the sample values are obtained from the continuous measurement), as well as embodiments in which discrete measurements are made repeatedly (whether periodically or intermittently) at a sufficient rate to allow the representative in-line value to be determined.

In exemplary embodiments, the sample sensor may be configured to extract a sample of the fluid from the flow of fluid during the event period using a sample extraction device—i.e. may be an on-line sensor.

As such, the on-line sensor may include a sample extraction device configured to extract the sample, and a sensing device configured to receive and analyse the sample. It should be appreciated that in exemplary embodiments the components of the sample extraction device and sensing device may be realised in a single unit. It is also envisaged that in an exemplary embodiment the sample sensor and the in-line sensor may be realised in a single unit.

The sample extraction device may include extraction means—for example one or more pumps, such as peristaltic pumps—to draw fluid from the fluid flow, and deliver it to the sensing device. The sample extraction device may include a sample collection chamber for conditioning the sample of fluid prior to delivery to the sensing device—for example by allowing settling of the fluid, and/or removal of a portion of the fluid. For example, in the analysis of a milk sample, air and milk bubbles rising to the top of the sample within the sample collection chamber may be removed, or permitted to exit.

The ability to analyse a sample of the fluid, rather than in-flow as with an in-line sensor, allows for use of sensing methodologies which are not currently viable for in-line sensors under conditions such as those experienced during (or required for) milking of an animal. For example, measurement techniques using ultrasound, acoustics, electromagnetic radiation (for example, near-infrared, or mid-infrared), and electronic impedance, are known for use in analysis of samples of milk, providing a higher precision determination of the targeted parameter. By way of example, the sensing device of the on-line sensor may implement the sensing methodology performed by the off-line Lacti-Check™ milk analyser by Page & Pedersen International, Ltd (www.pagepedersen.com) or the off-line MIRIS™ Dairy Milk Analyzer by Miris Holding AB (www.mirissolutions.com).

However, the analysis of a discrete sample has the potential to produce a value for a fluid parameter which is a poor representation of the value across the event period—particularly for fluid parameters that have significant variability across the event period. In the context of milking, the inventors have identified that fat content of milk is one such parameter. One possible way to address this limitation could be to obtain a proportional representative sample of the fluid across the event period. However, a sample collection device capable of collecting a proportional representative milk sample, that will function reliably without human intervention and clean itself effectively during the milking system wash, is believed to be likely to add substantial cost and complexity to the sensor. The inventors consider that such a sampler may be undesirable for these reasons. Further, this would require analysis of the sample at the end of milking—whereas it may be desirable to analyse the milk prior to this, in order to enable decision making regarding management of the animal, based on the analysis, prior to the animal exiting the milking facility.

In an exemplary embodiment, the distance between the in-line sensor and point of extraction of the sample along the fluid flow may be minimised such that the time for the fluid to flow between these points is insignificant for the purpose of determining the one or more in-line values corresponding to the sample value. However, it should be appreciated that reference to the one or more of the in-line values corresponding to the time of extracting the sample is intended to encompass embodiments in which the in-line sensor is positioned at a point along the fluid flow distal from the point of extraction of the sample, and the time for the fluid to flow between these points is of sufficient significance to be compensated for. In such an embodiment, the recorded time of the one or more in-line values may not match that of the sample value, but the values will be considered to correspond.

In an exemplary embodiment, the extraction of the sample may be performed on at least one condition being met during the event period. In an exemplary embodiment, the extraction of the sample may be performed at a predetermined time in the event period. It should be appreciated that reference to a predetermined time in the event period may include detection or prediction of conditions associated with the event period, rather than simply passage of a predetermined period of time. For example, it is known in the art of milking analysis to infer or determine a current stage of an individual animal's milking based on sensed parameters such as yield and flow rate, particularly in comparison with historical data associated with the animal. Further, determination of a suitable time for extraction of a sample may be made from a wider population—for example a fixed delay from the start of milking may approximate a suitable point in milking. In an exemplary embodiment, the sample value may be obtained between 30 to 120 seconds from the start of milking, once flow rate has reached a minimum threshold (for example, 1.5 litres per minute), and milk fat has reached a minimum threshold (for example, 3 g/100 mL).

In an exemplary embodiment, the sample may be extracted about the mid-point of the expected event period. The inventors consider that in the context of analysing milk, the mid-point of milking may have ancillary benefits in exemplary embodiments. For example, the instantaneous in-line milk fat measurement error at the mid-point of the milking may be most representative of the in-line milk fat measurement error of the whole cow milking. Further, where the sample sensor is capable of sensing a milk parameter such as protein and/or lactose content in addition to fat, it is believed that the mid-point of milking may be preferred for analysis of these parameters. While these parameters may not require determination of corrected representative values, it may still be of value to leverage the analytical capabilities of the sample sensor if they are available. However, it should be appreciated that this is not intended to be limiting to all exemplary embodiments of the present disclosure, and it is contemplated that the sample may be extracted at other times within the event period. Generally, it is envisaged that the sampling time may be selected to avoid low flow periods at the beginning and end of a milking. Further, in exemplary embodiments a plurality of samples may be extracted within the event period.

In an exemplary embodiment, extracting the sample of the fluid from the flow of fluid during the event period may include performing one or more rinses of the on-line sensor prior to collection of the volume of fluid to be analysed as the sample. Reference to a rinse should be understood to mean the processing of a volume of fluid through the on-line sensor, the rinse fluid being extracted from the fluid flow during the same event period as that being analysed as the sample. The inventors envisaged that this may assist with reducing the likelihood of contamination of the sample by the sample of the previous event period.

However, because the fat content changes during a cow milking, the milk in each rinse will have a different fat content. In exemplary embodiments in which extraction of the sample involves two rinses and a final sample, a fraction of the milk of the first rinse will be mixed with the milk of the second rinse, and a fraction of the milk of the second rinse will be mixed with the milk of the final sample. The final sample will have a fat content comprised of the two rinses and the final sample. To account for this, in exemplary embodiments, the in-line value of the fluid parameter corresponding to the time of extracting the sample may be a weighted average of the in-line values at the time of the rinses and final sample, with the later obtained in-line values given a higher weighting. It is envisaged that this may assist with accounting for variation in the fluid parameter during collection of the sample.

By way of example in the context of milk analysis, where performing two rinses and a final sample, the in-line value of the fluid parameter corresponding to the time of extracting the sample may be: $P = x \cdot V_3 + y \cdot V_2 + z \cdot V_1$, where P is the sample in-line value, $V_n$ is the in-line value at the time of the rinses and final sample, and (x, y, z) are the relative weightings and x>y>z.

In an exemplary embodiment, 'x' may be between 0.8 and 0.9, 'y' may be between 0.09 and 0.16, and 'z' may be between 0.01 and 0.04. It should be appreciated that these values are not intended to be limiting to all exemplary embodiments, as it is contemplated that these may be influenced by factors such as the type of fluid being measured, and characteristics of the sample sensor such as geometry and sensor transducer type and/or materials.

Determination of the representative in-line value of the fluid parameter across the event period, based at least in part on the plurality of in-line values, may be made using any suitable technique known in the art. For example, the representative in-line value may be an average of the plurality of in-line values. In particular, the representative in-line value may be a weighted average, and more particularly weighted by the flow rates corresponding to the in-line values. In exemplary embodiments, the representative value may be determined from discrete in-line values, or by interpolation between discrete in-line values. In exemplary embodiments, the representative in-line value may be determined cumulatively throughout the milking, or at the end of the milking. In an exemplary embodiment in which the in-line value is continuously measured, this measurement may be integrated or averaged to determine the representative value.

The inventors have identified that the difference between the in-line value of the fluid parameter corresponding to the time of extracting the sample, and the value of the fluid parameter as determined by a higher precision analysis, is relatively consistent across the event period. With the sample value providing a higher precision measurement than the in-line value, this allows for an overall representative value of the fluid parameter across the event period to be determined using an error correction value based on the assumption that the measurement error of the in-line sensor is relatively consistent across the event period. This overall representative value may be, for example a correction of error in the in-line values across the event period (or the representative in-line value) to obtain the corrected representative value of the fluid parameter. However it should be appreciated that the overall representative value may not result from correcting error in one of the sensor values as such, while still having greater accuracy than the representative in-line value. For example, an estimated average value of the fluid parameter over the event period may be obtained through adjustment of the sample value of the fluid parameter by an error correction value based on a relationship between the in-line value of the fluid parameter corresponding to the time of extracting the sample and the representative in-line value of the fluid parameter across the event period.

For completeness, it should be appreciated that reference to correction of error is intended to mean an improvement in the accuracy of the determination of the fluid parameter in comparison with that determined from the in-line sensor alone.

It should be appreciated that in exemplary embodiments this difference (i.e. that between the in-line value of the fluid parameter corresponding to the time of extracting the sample, and the value of the fluid parameter as determined by a higher precision analysis) may be expressed as an absolute difference or error, or a relative difference or error.

In an exemplary embodiment, determination of the corrected representative value of the fluid parameter includes: determining a difference between the in-line value of the fluid parameter corresponding to the time of extracting the sample, and the sample value of the fluid parameter; and adjusting the representative in-line value of the fluid parameter across the event period by the determined difference.

By way of example in the context of milk analysis, if the in-line value of milk fat corresponding to the time of extracting the sample was 4.8 g/100 mL, and the sample value of the fluid parameter was 4.0 g/100 mL, the difference would be −0.8 g/100 mL (the difference being indicative of the measurement error of the in-line sensor). If the representative in-line value of the fluid parameter across the event period was 5.8 g/100 mL, the corrected representative value of the fluid parameter would be 5.8+(−0.8)=5.0 g/100 mL.

In an exemplary embodiment, determination of the estimated average value of the fluid parameter includes: determining a difference between the in-line value of the fluid parameter corresponding to the time of extracting the sample, and the representative in-line value of the fluid parameter across the event period; and adjusting the sample value of the fluid parameter by the determined difference.

By way of example in the context of milk analysis, if the in-line value of milk fat corresponding to the time of extracting the sample was 4.8 g/100 mL, and the representative in-line value of the fluid parameter across the event period was 5.8 g/100 mL, the difference would be +1.0 g/100 mL. If the sample value of the fluid parameter was 4.0 g/100 mL, the corrected representative value of the fluid parameter would be 4.0+1.0=5.0 g/100 mL.

In an exemplary embodiment, determination of the corrected representative value of the fluid parameter includes: determining a relative difference between the in-line value of the fluid parameter corresponding to the time of extracting the sample, and the sample value of the fluid parameter; and adjusting the representative in-line value of the fluid parameter across the event period with the relative difference.

In an exemplary embodiment, determination of the estimated average value of the fluid parameter includes: determining a relative difference between the in-line value of the fluid parameter corresponding to the time of extracting the sample, and the representative in-line value of the fluid parameter across the event period; and adjusting the sample value of the fluid parameter with the relative difference.

For a firmware and/or software (also known as a computer program) implementation, the techniques of the present disclosure may be implemented as instructions (for example, procedures, functions, and so on) that perform the functions described. It should be appreciated that the present disclosure is not described with reference to any particular programming languages, and that a variety of programming languages could be used to implement the present invention. The firmware and/or software codes may be stored in a memory, or embodied in any other processor readable medium, and executed by a processor or processors. The memory may be implemented within the processor or external to the processor.

A processor may be a microprocessor, but in the alternative, the processor may be any processor, controller, microcontroller, state machine, or cloud computing device known in the art. A processor may also be implemented as a combination of computing devices, for example, a combination of a digital signal processor (DSP) and a microprocessor, a plurality of microprocessors, one or more microprocessors in conjunction with a DSP core, or any other such configuration.

The processors may function in conjunction with servers and network connections as known in the art. By way of example, the on-line and sample sensors and a central processor may communicate with each other over a Controller Area Network (CAN) bus system. In the context of milking, other performance sensors (for example flow or yield sensors), animal identification devices, and milking plant sensors may also communicate with the central processor. In an exemplary embodiment, animal identifiers, data from the sensors, and any other data may be stored in a data cloud.

The steps of a method, process, or algorithm described in connection with the present disclosure may be embodied directly in hardware, in a software module executed by one or more processors, or in a combination of the two. The various steps or acts in a method or process may be performed in the order shown, or may be performed in another order. Additionally, one or more process or method steps may be omitted or one or more process or method steps may be added to the methods and processes. An additional step, block, or action may be added in the beginning, end, or intervening existing elements of the methods and processes.

BRIEF DESCRIPTION OF DRAWINGS

Further aspects of the present invention will become apparent from the following description which is given by way of example only and with reference to the accompanying drawings in which:

FIG. 9 is a plot of representative in-line sensor values against laboratory test values.

DETAILED DESCRIPTION

Exemplary embodiments are discussed herein in the context of analysis of milk. However, it should be appreciated that principles of the disclosure discussed herein may be applied to the analysis of other fluids.

Figure 1A:
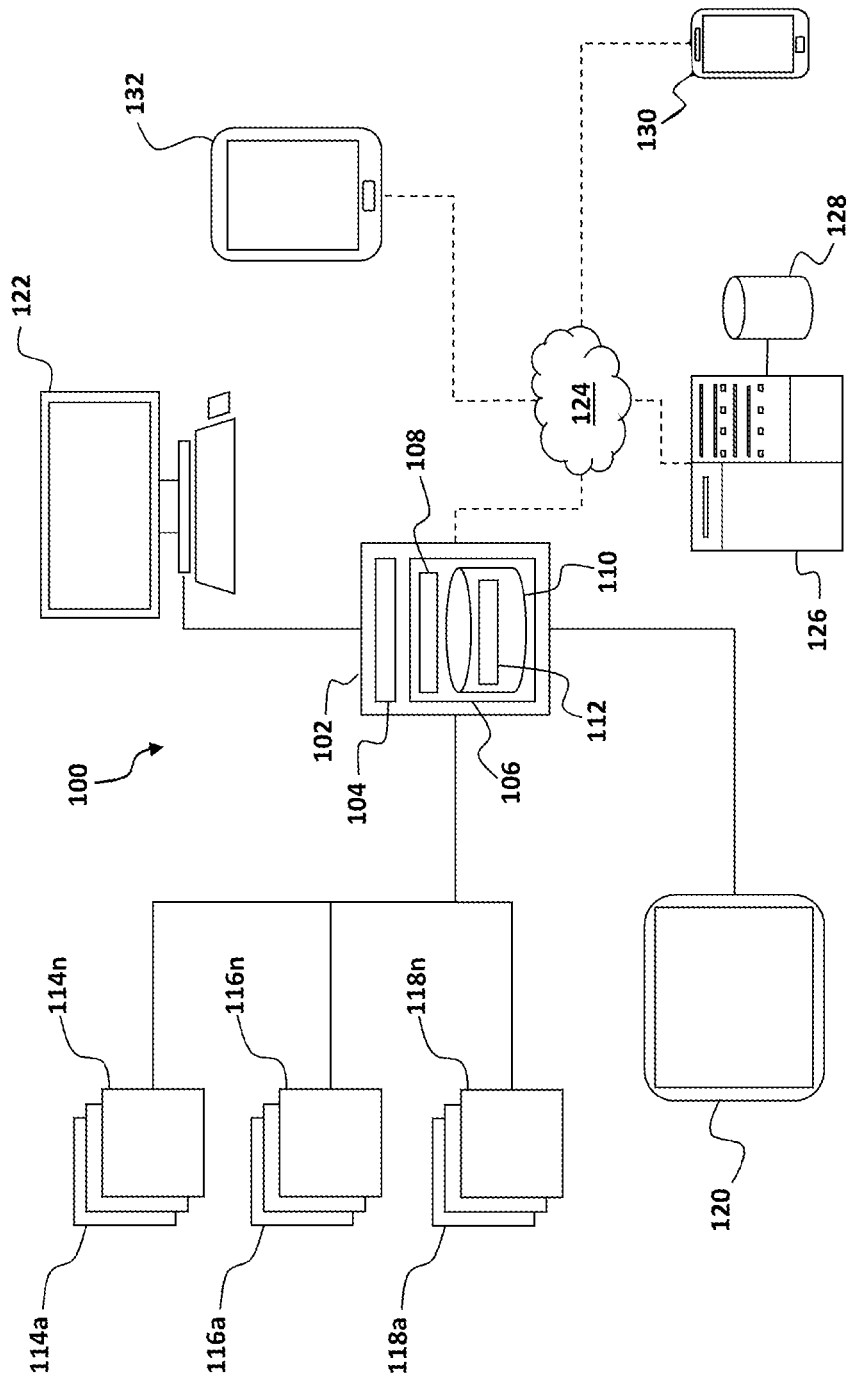
FIG. 1A is a schematic diagram of an exemplary livestock management system in which an aspect of the present disclosure may be implemented.

FIG. 1A illustrates a livestock management system 100, within which a local hardware platform 102 manages the collection and transmission of data relating to operation of a milking facility. The hardware platform 102 has a processor 104, memory 106, and other components typically present in such computing devices. In the exemplary embodiment illustrated the memory 106 stores information accessible by processor 104, the information including instructions 108 that may be executed by the processor 104 and data 110 that may be retrieved, manipulated or stored by the processor 104. The memory 106 may be of any suitable means known in the art, capable of storing information in a manner accessible by the processor 104, including a computer-readable medium, or other medium that stores data that may be read with the aid of an electronic device. The processor 104 may be any suitable device known to a person skilled in the art. Although the processor 104 and memory 106 are illustrated as being within a single unit, it should be appreciated that this is not intended to be limiting, and that the functionality of each as herein described may be performed by multiple processors and memories, that may or may not be remote from each other. The instructions 108 may include any set of instructions suitable for execution by the processor 104. For example, the instructions 108 may be stored as computer code on the computer-readable medium. The instructions may be stored in any suitable computer language or format. Data 110 may be retrieved, stored or modified by processor 104 in accordance with the instructions 110. The data 110 may also be formatted in any suitable computer readable format. Again, while the data is illustrated as being contained at a single location, it should be appreciated that this is not intended to be limiting—the data may be stored in multiple memories or locations. The data 110 may also include a record 112 of control routines for aspects of the system 100.

The hardware platform 102 may communicate with various devices associated with the milking facility, for example: in-line sensors 114a to 114n associated with individual milking clusters within the milking facility, and sample sensors in the form of on-line sensors 116a to 116n associated with the individual milking clusters.

Animal identification devices 118a to 118n are provided for determining an animal identification ("animal ID") of individual animals entering, or within, the milking facility. More particularly, the animal identification devices 118a to 118n may be used to associated an animal ID with each of the milking clusters associated with the in-line sensors 114a to 114n and on-line sensors 116a to 116n, such that the sensor data may be attributed to the individual animals. A variety of methodologies are known for the determination of an animal ID—for example a radio frequency identification ("RFID") reader configured to read a RFID tag carried by the animal. In an alternative embodiment, or in conjunction with the animal identification devices 118a to 118n, a user may manually enter (or correct) animal IDs via a user device—examples of which are discussed below.

The hardware platform 102 may also communicate with user devices, such as touchscreen 120 located within the milking facility for monitoring operation of the system, and a local workstation 122. The hardware platform 102 may also communicate over a network 124 with one or more server devices 126 having associated memory 128 for the storage and processing of data collected by the local hardware platform 102. It should be appreciated that the server 126 and memory 128 may take any suitable form known in the art—for example a "cloud-based" distributed server architecture. The network 124 potentially comprises various configurations and protocols including the Internet, intranets, virtual private networks, wide area networks, local networks, private networks using communication protocols proprietary to one or more companies—whether wired or wireless, or a combination thereof. It should be appreciated that the network 124 illustrated may include distinct networks and/or connections: for example a local network over which the user interface may be accessed within the vicinity of the milking facility, and an internet connection via which the cloud server is accessed. Information regarding operation of the system 100 may be communicated to user devices such as a smart phone 130 or a tablet computer 132 over the network 124.

Figure 1B:
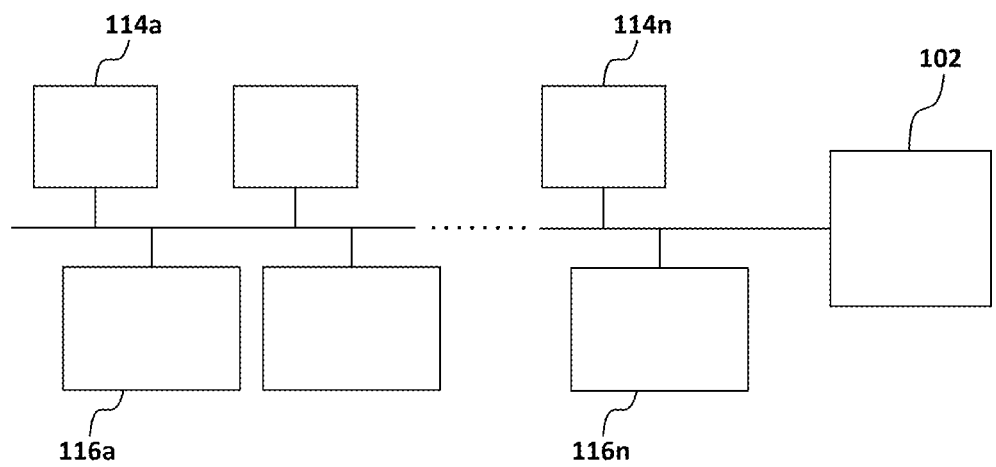
FIG. 1B is a schematic diagram of an exemplary sensor arrangement associated for use in the exemplary livestock management system.

FIG. 1B illustrates the in-line sensors 114a to 114n and on-line sensors 116a to 116n connected over a Controller Area Network (CAN) bus with the hardware platform 102. It should be appreciated that while not illustrated, additional performance sensors (for example performance sensors such as milk flow or yield sensors) may also be connected to, and communicate over, the CAN bus. Each of the in-line sensors 114a to 114n and on-line sensors 116a to 116n is associated with an individual milking cluster in the milking facility—i.e. the sensor data output by an individual sensor relates to milk from an individual animal. In exemplary embodiments, sensors may be provided for each milking cluster in the milking facility. However, it should be appreciated that this is not intended to be limiting to every embodiment of the present disclosure. For example, it is contemplated that only a subset of milking clusters may have associated sensors (e.g. 1 in 4).

In an exemplary embodiment, the in-line sensor 114 may be configured to determine at least the fat content of milk—for example the YieldSense™ volume, fat, and protein sensor by LIC Automation Limited, or the AfiLab™ fat, protein and lactose concentration sensor by Afimilk Ltd. It should be appreciated that while the inventors have identified the present disclosure as having particular application to analysis of fat, this is not intended to be limiting to all embodiments of the present disclosure.

In an exemplary embodiment, the on-line sensor 116 may implement an ultrasound based sensing methodology as performed by the off-line LactiCheck™ milk analyser by Page & Pedersen International, Ltd or a mid-infrared based sensing methodology as performed by the off-line MIRIS™ Dairy Milk Analyzer by Miris Holding AB. Further, while the sample sensor is described in the context of being an on-line sensor, it should be appreciated that the present disclosure may have application to embodiments in which the sample is analysed by an off-line sensor.

Figure 2:
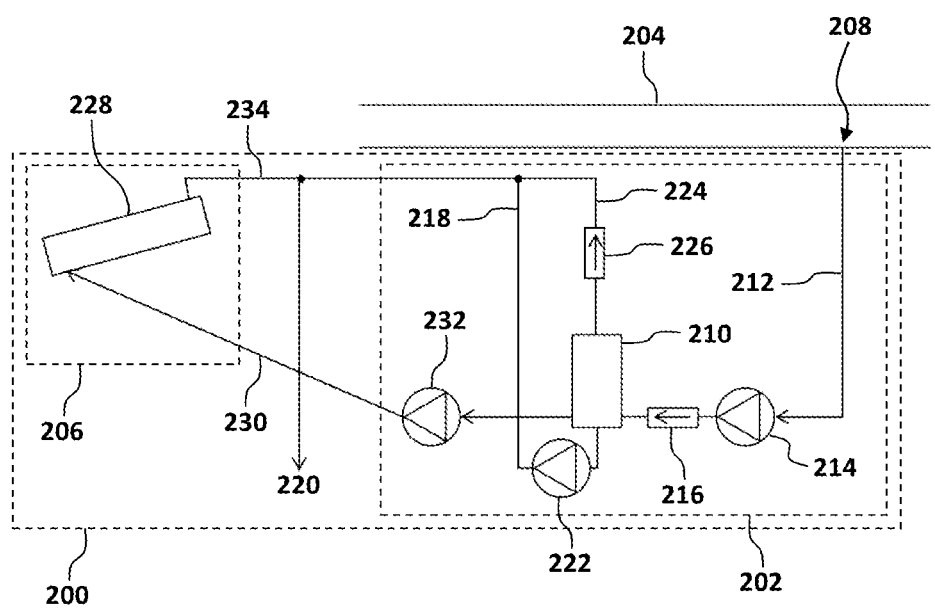
FIG. 2 is a schematic diagram of an exemplary on-line sensor according to one aspect of the present disclosure.

Referring to FIG. 2, an exemplary on-line sensor 200 is illustrated, which may be used as the on-line sensors 116a to 116n. In this exemplary embodiment, the on-line sensor 200 includes a sample extraction device 202 configured to extract a sample of milk from a milk tube 204 through which milk flows, and a sensing device 206 configured to receive and analyse the sample. It should be appreciated that in exemplary embodiments the milk tube 204 may be a component of the on-line sensor 200—for example a section of tube configured to be connected in-line with the long milk tube of a milking cluster.

An off-take 208 in the milk tube 204 is connected to a sample chamber 210 via a first sample tube 212. A first peristaltic pump (herein referred to as sample pump 214) is provided on the first sample tube 212 to draw milk from the off-take 208 to the sample chamber 210, with a first non-return valve 216 preventing milk from being drawn back from the sample chamber 210. The sample chamber 210 may include electrodes measuring conductivity to permit detection of a fill level of the sample chamber 210.

A sample waste tube 218 connects the sample chamber 210 to waste 220, with an associated second peristaltic pump (herein referred to as waste pump 222) provided to draw milk from the sample chamber 210 to waste 220. An air bleed tube 224 having a second non-return valve 226 connects to the top of the sample chamber to permit escape of air during filling of the sample chamber 210. A third non-return valve (not illustrated in FIG. 2) is located in the wall of the sample chamber 210 to permit air to be drawn into the chamber when the waste pump 222 (or sensor pump 232, see below) are running.

In this exemplary embodiment, the sensing device 206 includes a sensor cell 228 configured to perform ultrasound based measurements of milk contained therein. For example, the sensor cell 228 may be the ultrasound sensing cell of the LactiCheck™ milk analyser. A sample delivery tube 230 is connected near or at the bottom of the sample chamber 210 and connects the sample chamber to the sensor cell 228. A third peristaltic pump (herein referred to as sensor pump 232) is provided to deliver milk to the sensor cell 228 from the sample chamber 210. A sensor waste tube 234 connects the sensor cell 228 to waste 220.

While not illustrated in FIG. 2, it should be appreciated that one or more controllers may be used to control the operation of the various components described, receive data obtained by the sensor cell 228, and communicate over a network such as the CAN bus of FIG. 113.

Figure 3:
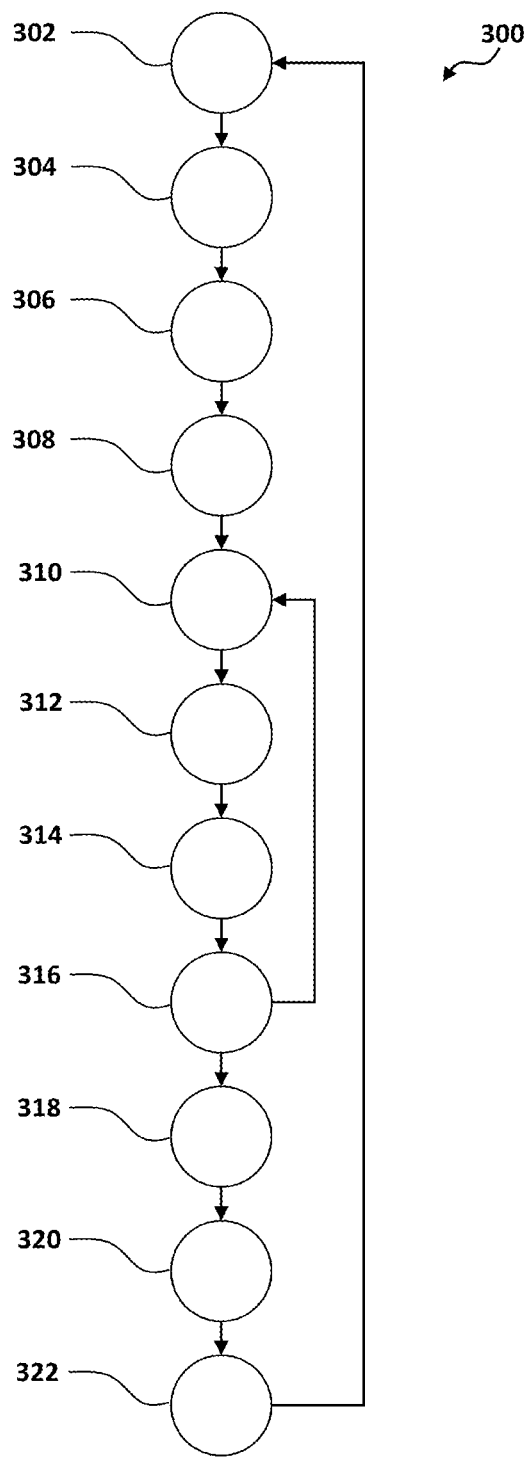
FIG. 3 is a state machine diagram for operation of the exemplary on-line sensor according to one aspect of the present disclosure.

FIG. 3 illustrates a state machine diagram 300 for control of the on-line sensor 200. In idle state 302, the on-line sensor 200 awaits a signal that milking has started. In first state 304, the on-line sensor 200 receives a signal that indicates that milking has started (for example, from the in-line sensor 114), and initiates a delay timer before transitioning to the second state 306 on expiry of the timer. In an alternate embodiment, the signal may indicate a predetermined point in milking—for example the mid-point—and the state machine may proceed to the second state 306 without use of a delay timer.

In second state 306, the waste pump 222 is operated for a predetermined period of time to remove residual milk from the sample chamber 210. In third state 308 the waste pump 222 and sensor pump 232 are operated for a predetermined period of time to remove residual milk from the sensor cell 228 and associated sample delivery tubes.

In fourth state 310 the sample pump 214 and waste pump 222 are operated to draw milk from the milk tube 204 via the offtake 208. The milk is pumped through the sample chamber 210 to the waste tube 218 to remove any milk from the previous milking which remains in the first sample tube 212. The new milk also provides a rinsing effect of the waste tube 218 between the sample chamber 210 and waste 220.

In fifth state 312, to collect a sample the sample pump 214 is run (with the waste pump 222 and sensor pump 232 stopped) until the milk fills the sample chamber 210 to the fill level (as detected by electrodes). In sixth state 314 a time delay (for example about 1 second) allows air in the milk to escape via rising to the top of the sample, as the accuracy of ultrasound measurements can be affected by bubbles in the sample.

In the seventh state 316 the sample is then withdrawn from the sample chamber 210 by operating the sensor pump 232 for a predetermined period of time to rinse the sample delivery tube 230 and sensor cell 228 and deliver a slug of milk to fill the sensor cell 228.

In an exemplary embodiment, states 310 to 316 may be repeated one or more times—for example three times—in order to rinse the on-line sensor 200 to reduce the effect of cross-contamination from residual milk from the previous milking.

In eight state 318, analysis of the milk in sensor cell 228 is initiated. In ninth state 320, the on-line sensor 200 waits for the results of the analysis.

In tenth state 322, the results of the analysis are obtained, at which time the waste pump 222 and sensor pump 232 are operated to deliver the current sample to waste 220.

Figure 4:
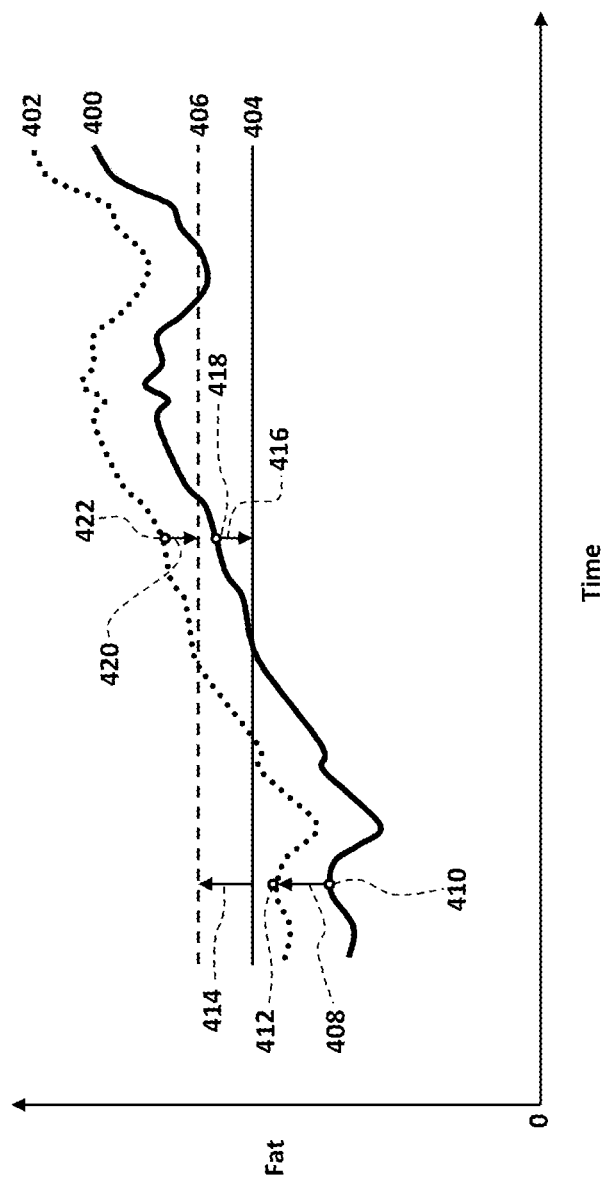
FIG. 4 is a graph illustrating the relationship between values of fat content of milk determined by an in-line sensor and an on-line sensor over time.

FIG. 4 is a graph of idealised fat content measurements of milk versus time for the purposes of understanding a principle of operation of an aspect of the present disclosure. First plot 400 is representative of an output over time of an in-line YieldSense™ volume, fat, and protein sensor by LIC Automation Limited. Second plot 402 is an approximation of measurements of spot samples extracted from the same flow of milk being analysed by the YieldSense™ sensor, and analysed using a higher precision sensor such as the off-line LactiCheck™ milk analyser by Page & Pedersen International, Ltd.

First line 404 illustrates the fat content across the entire milking, based on the YieldSense™ measurements—for example a weighted average of the first plot 400 (weighted by flow rates at times corresponding to the instant measurements), herein referred to as the "in-line average fat". For completeness, it should be appreciated that the representative fat content 404 may be obtained by means other than a weighted average. Second line 406 illustrates fat content as determined from a higher precision measurement, herein referred to as the "actual fat". By way of example, the higher precision measurement may be obtained by way of laboratory testing of a sample of milk collected from a vessel in which milk from the entire milking is collected, and mixed prior to collection of the sample.

The inventors have identified that the error 408 between a YieldSense™ measurement 410 and a LactiCheck™ measurement 412 at a particular point of time is representative of the error 414 between the in-line average fat 404 and the actual fat 406.

As a result, in principle a corrected value of the in-line average fat 404 may be obtained to better approximate the actual fat 406—for example by adjusting the in-line average fat 404 by the error 414, or by determining a relative error and correcting the in-line average fat 404 accordingly.

Alternatively, the difference 416 between a point 418 on the first plot 400 and the in-line average fat 404 is representative of the difference 420 between a corresponding point 422 of the second plot 402 and the actual fat 406. As such, an approximation or estimation of the actual fat 406 may be obtained by adjusting the point 422 value by the difference 420. Again, it should be appreciated that a determination of relative error may be used to make this correction.

Figure 5:
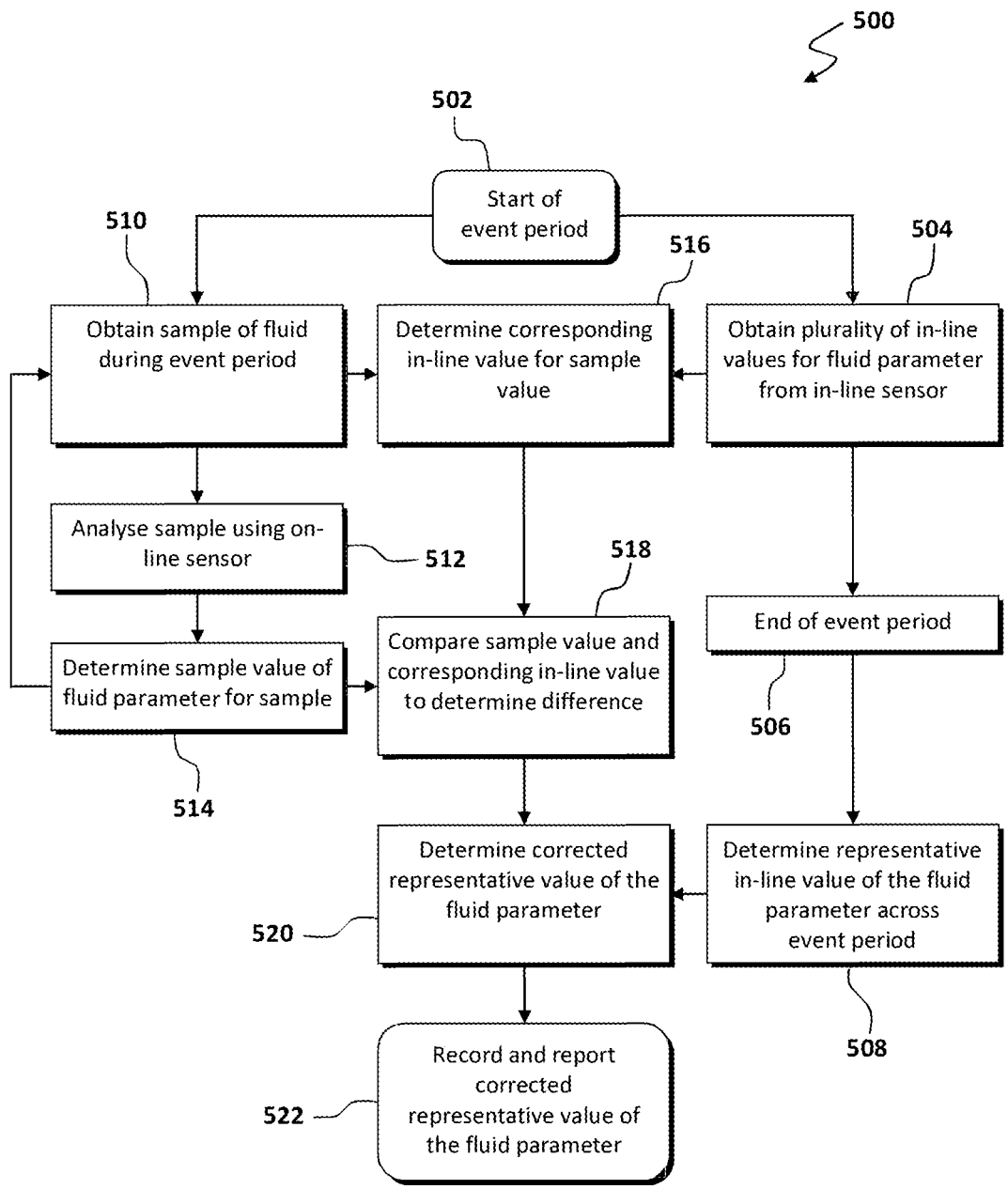
FIG. 5 is a flow diagram illustrating a first exemplary method of determining a representative in-line value of a fluid parameter across an event period.

FIG. 5 illustrates a method 500 of determining a corrected representative value of a fluid parameter—for example fat content of milk. In step 502, an event period is started, for example a milking session of an individual animal. The start of the event period may be detected, for example, by the in-line sensor 114 (or another in-line sensor) detecting the start of a flow of milk, and a signal sent to the associated on-line sensor 116.

In step 504, the in-line sensor 114 obtains a plurality of measurements of the milk (the "in-line values") flowing past the in-line sensor 114. Such measurements will herein be referred to as occurring continuously, but it should be apparent to a person skilled in the art of data collection and analysis that this is not intended to exclude embodiments in which discrete measurements are made repeatedly (whether periodically or intermittently) at a sufficient rate to represent a continuous measurement. For example, a YieldSense™ measurement being used as an "in-line value" may be a value representative of a plurality of instantaneous measurements over a relatively short period of time (for example, the preceding 5 seconds) in comparison with the time to extract and analyse a sample with an on-line sensor 116 (for example, in the order of 120 seconds. Such in-line values may be transmitted to a processing resource shared with the on-line sensor 116, such as the hardware platform 102, including a time at which the in-line value was obtained.

The in-line values are measured until the end of the event period (for example, end of milking) in step 506. In step 508, a representative in-line value of the fluid parameter across the event period is determined (for example, in-line average fat 404 of FIG. 4) and transmitted to the shared processing resource.

In step 510, following detection of the start of the event period in step 502, the on-line sensor 116 obtains a sample of the milk. In an exemplary embodiment, the sample is extracted after a predetermined period of time—for example a period of time after which a mid-point of the milking is expected. In step 512 the sample is analysed by the on-line sensor 116, and in step 514 a "sample value" of the targeted parameter (for example, fat content) is determined and transmitted to the shared processing resource, including a time at which the sample was extracted. In exemplary embodiments, steps 510 to 514 may be repeated to obtain more than one sample value during the event period.

In step 516, for each sample value the shared processing resource determines one or more corresponding in-line values, based on timing of the in-line values and the extraction of the sample. In exemplary embodiments—described further below with reference to FIG. 7 and FIG. 8—the corresponding in-line value may be determined based on a plurality of in-line values obtained during collection of the sample, herein referred to as a "sample in-line value".

In step 518, a comparison of the sample value and corresponding in-line value (or sample in-line value) is made to determine the difference between them—the difference being indicative of the error of the in-line values across the milking (whether absolute or relative).

In step 520, a corrected representative value of the fluid parameter (for example, a corrected value of the in-line average fat 404) is determined based on the determined error. For example, the representative in-line value determined in step 508 may be adjusted by the absolute error.

In step 522 the corrected representative value for that event period is stored—for example in memory 106 of the hardware platform 102, and/or memory 128 associated with the server 126. It should be appreciated that the corrected representative value may be stored against a record for an individual animal determined as being the source from which the analysed milk was extracted. Further, alerts or further actions may be determined on the basis of the received value—as known in the art.

Figure 6:
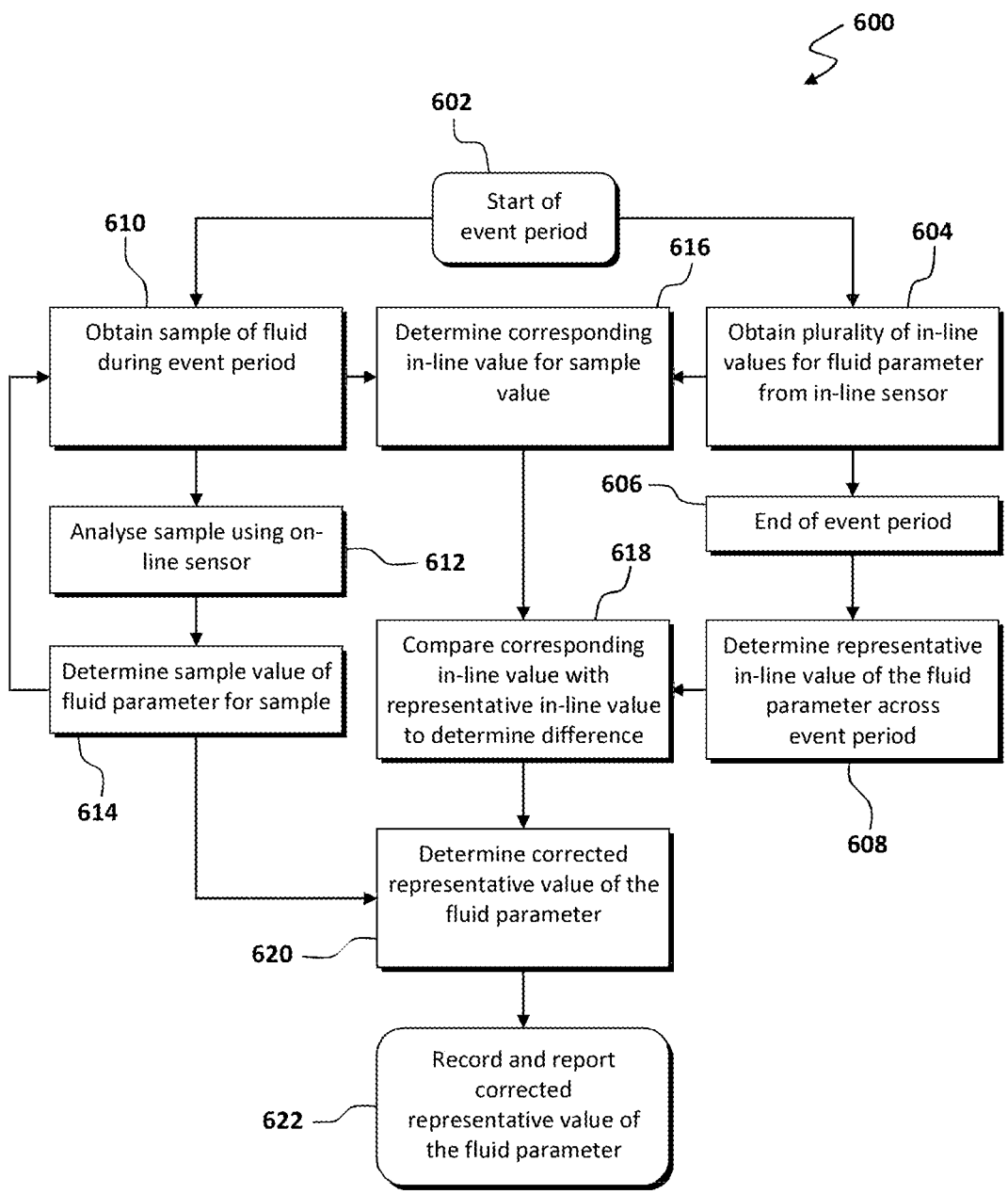
FIG. 6 is a flow diagram illustrating a second exemplary method of determining a representative in-line value of a fluid parameter across an event period.

FIG. 6 illustrates another method 600 of determining a corrected representative value of a fluid parameter—for example fat content of milk. Steps 602 to 616 are substantially equivalent to steps 502 to 516 of method 500 as described above.

However, in step 618 the in-line value (or the sample in-line value) corresponding to the sample value is compared with the representative in-line value (for example, in-line average fat 404 of FIG. 4) to determine the difference between them—being indicative of the difference between the sample value and the corrected representative value of the fluid parameter. This difference may be determined, for example, in absolute or relative terms.

In step 620, the sample value is adjusted based on the determined difference between the in-line value and the representative in-line value to produce an estimated representative value. For example, the sample value may be adjusted by the absolute difference. In step 622 the estimated representative value for that event period is be stored and actioned as required.

Figure 7:
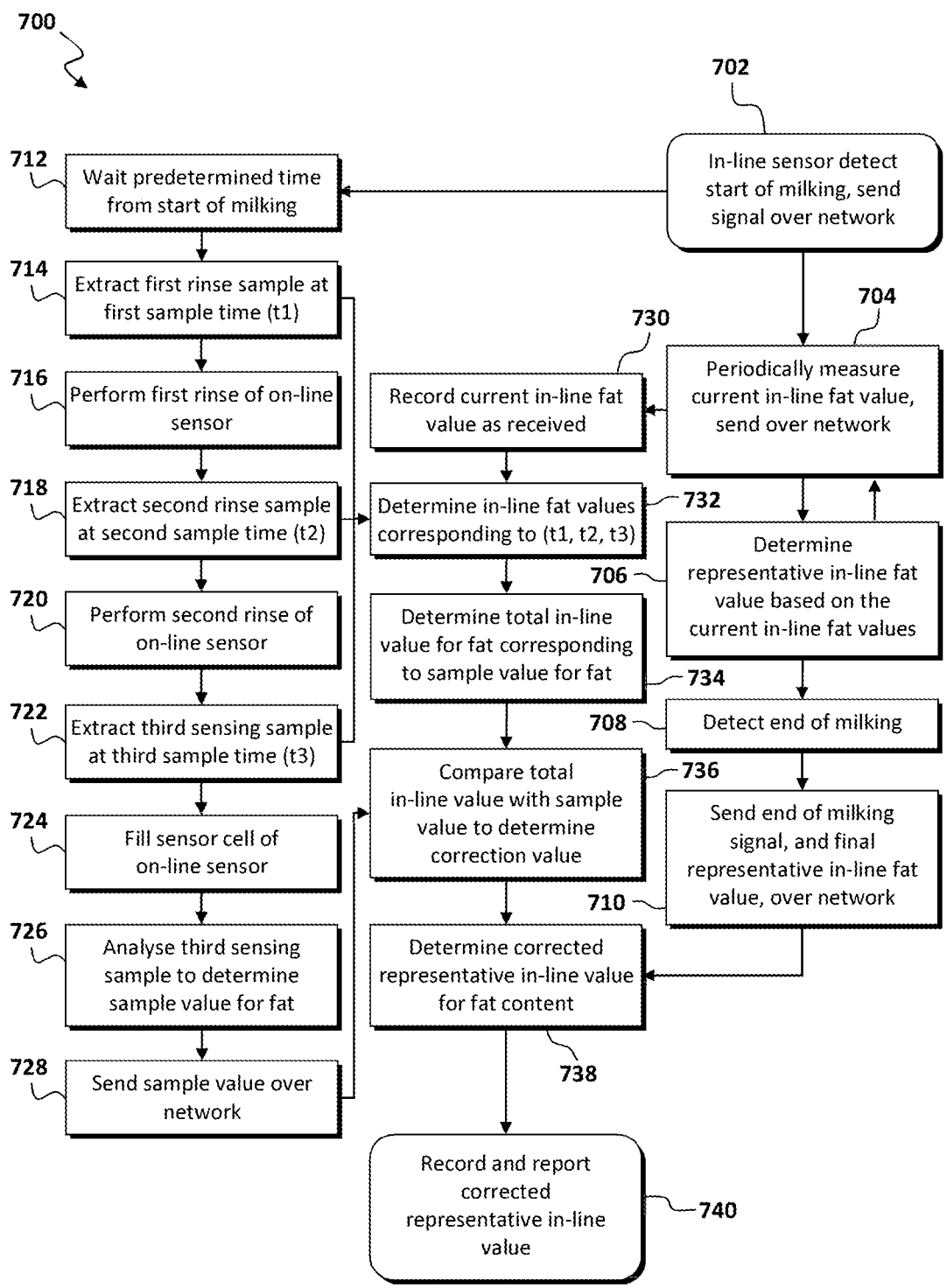
FIG. 7 is a flow diagram illustrating an exemplary method of determining a representative in-line value of fat content of milk extracted from a milking animal across a milking period.

FIG. 7 illustrates an exemplary method 700 of determining a corrected representative value of a fluid parameter—for example fat content of milk—in which a rinsing procedure is performed for the on-line sensor 116 to reduce the effects of cross-contamination (for example, repetition of states 308 to 316 of FIG. 3). In such an embodiment, the corresponding in-line value may be a weighted combination of in-line values. For example, in an embodiment in which two rinses are performed before collecting the sample for analysis, the in-line value ("sample in-line value") determined to correspond to the extraction of the sample may be determined as follows: $P = x \cdot V_3 + y \cdot V_2 + z \cdot V_1$, where P is the sample in-line value, $V_n$ is the in-line value at the time of extracting the rinses and final sample, and (x, y, z) are the relative weightings and x>y>z.

By way of example, the values of (x, y, z) may be (0.86, 0.12, 0.02). However, it should be appreciated that the values of (x, y, z) may be influenced by the configuration of the on-line sensor, such as the volume of the lines and chambers/cells exposed to milk during sample extraction and analysis, and these values may be derived for a particular sensor configuration. Method 700 is described with particular reference to the in-line sensor being a YieldSense™ sensor 114, the on-line sensor being on-line sensor 200 with the sensing device 206 performing ultrasound analysis using a LactiCheck™ sensor, and the fluid parameter being milk fat content.

In step 702, the YieldSense™ sensor 114 detects the start of milking, and sends a milking start signal over the network (for example, the CAN bus of FIG. 1B) to an associated on-line sensor 200 and hardware platform 102. In step 704, the YieldSense™ sensor 114 periodically determines a current in-line fat value and transmits this to the hardware platform 102—for example every 5 seconds. In step 706 the YieldSense™ sensor 114 determines a representative in-line fat value based on the current in-line fat values obtained during the milking—for example a cumulative average weighted by flow rate. In step 708 the YieldSense™ sensor 114 detects the end of milking, and in step 710 transmits this over the network together with the final representative in-line fat value.

In step 712, on receiving the signal from the YieldSense™ sensor 114 indicating the start of milking, the on-line sensor 200 waits for a predetermined period of time. In step 714, the sample extraction device 202 extracts a first rinse sample from the milk tube at a first sample time (t1), and rinses the sensing device 206 in step 716. In step 718, the sample extraction device 202 extracts a second rinse sample from the milk tube at a second sample time (t2), and rinses the sensing device 206 in step 720. In step 722, the sample extraction device 202 extracts a third sensing sample from the milk tube at a third sample time (t3), and fills the sensor cell 228 in step 724. In step 726, the analysis of the third sensing sample is performed, and a sample value of fat content determined. In step 728 the sample value is transmitted over the network.

In step 730, the current in-line fat values from the YieldSense™ sensor 114 are recorded as they are received—for example by the hardware platform 102. In step 732, at each of steps 714, 718, and 722, the current in-line fat values at the times of extracting the respective samples (t1, t2, t3) are recorded. The times (t1, t2, t3) may be determined, for example, by using the associated state transition described in FIG. 3.

In step 734, a sample in-line value (P) of fat content for the third sensing sample of milk is determined using: $P = 0.86 \cdot V_3 + 0.12 \cdot V_2 + 0.02 \cdot V_1$. In step 736, a correction value is determined based on a comparison of the sample value and the sample in-line value, or the sample in-line value and the final representative in-line value provided by the YieldSense™ sensor 114 in step 710.

In step 738 an overall representative fat content value—i.e. a representation of the average fat content of milk extracted across the course of the milking—is determined based on the correction value determined in step 736.

In one embodiment, where the correction value is the difference between the sample value and the sample in-line value, a corrected representative fat content value may be determined by adjusting the final representative in-line fat value from the YieldSense™ sensor 114 by the correction value (for example, as described in relation to method 500).

In another embodiment, where the correction value is the difference between the sample in-line value and the final representative in-line value, an estimated representative fat content value may be determined by adjusting the sample value from the on-line sensor 200 by the correction value (for example, as described in relation to method 600).

In step 740 the overall representative fat content value is stored, and reported and/or actioned as required.

Figure 8:
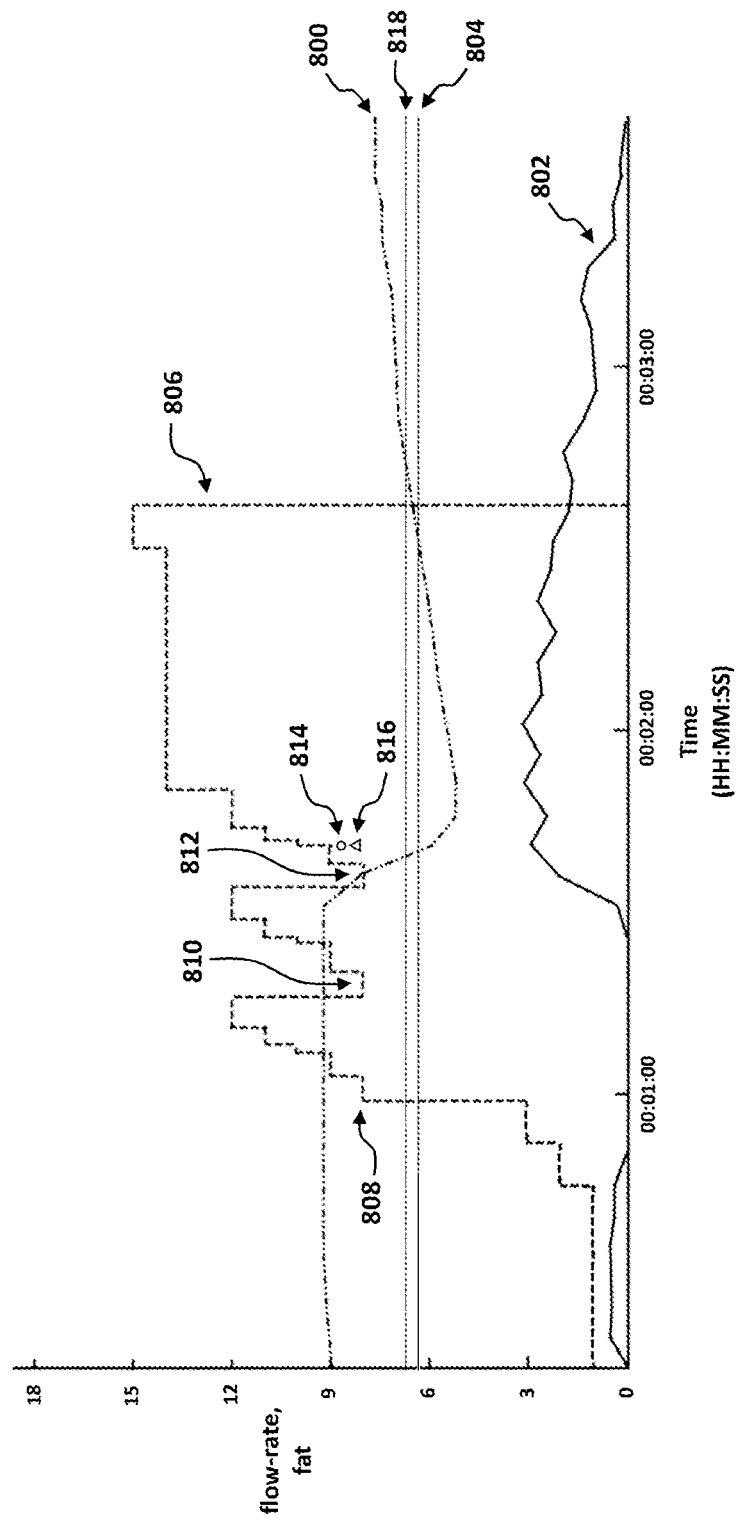
FIG. 8 is a graph illustrating the performance of the exemplary method of determining a representative in-line value of fat content of milk.

FIG. 8 is a graph illustrating implementation of the method 700. First plot 800 shows the in-line values of fat content determined by a YieldSense™ sensor based on a weighted average of instantaneous measurements over a 5 second period—weighted by the flow rate of the milk (illustrated by second plot 802). A representative in-line fat content value based on the in-line values is shown by line 804. It is noted that the trend in fat content illustrated in plot 800 is not that expected for typical milking—more particularly there is a drop in fat in the course of the milking, while this would normally be expected to rise over the same period.

Dashed line 806 represents the current state of the on-line sensor 200 over time—including the first rinse sample 808, second rinse sample 810, and the sensing sample 812. The sample fat value 814 is compared with the sample in-line fat value 816 to determine a measurement error for this milking session. A corrected representative in-line fat content value is derived by adding the measurement error to the representative in-line fat content value 804, which approximates a laboratory determined fat content value 818 (for example, based on a sample from a vessel in which milk from across the milking is mixed).

FIG. 9 is a plot demonstrating outcomes of implementing the present disclosure. The plot shows the results for 92 milkings of 20 cows over five days. A first series 900 having a first linear relationship 902 compares the fat content (in g/100 mL) obtained by an in-line YieldSense sensor with a higher precision laboratory method performed on a bucket sample taken at the end of each milking. A second series 904 having a second linear relationship 906 compares the corrected fat content with the laboratory method. In this example, the corrected fat content was obtained by correcting the YieldSense value using method 600, more particularly using absolute error in step 620, with the final sample being taken at a time approximately 25 to 40 percent through the milking time using a fixed delay time in step 304 of the state machine in FIG. 3.

It may be seen in comparison with the 1:1 line 908 that the plot shows a significant improvement in systematic error. However, the inventors consider that the improvement of standard deviation of error (from 0.608 g/100 mL to 0.283 g/100 mL) may be particularly advantageous, compensating for errors in the YieldSense measurement which may vary from milking to milking. The entire disclosures of all applications, patents and publications cited above and below, if any, are herein incorporated by reference.

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

Aspects of the present invention have been described by way of example only and it should be appreciated that modifications and additions may be made thereto without departing from the scope thereof.

The invention claimed is:

1. A system for analyzing a fluid, comprising:
an in-line sensor configured to analyze a fluid flowing past the in-line sensor to determine at least one in-line value of a fluid parameter of the fluid across an event period;
a sample sensor comprising a sample extraction device configured to extract fluid from the flow of fluid, and a sensing device configured to receive and analyze the extracted fluid, wherein the sample sensor is configured to:
perform one or more rinses of the sensing device with fluid extracted from the flow of fluid, prior to extraction of a volume of the fluid to be analyzed as a sample; and
analyze the sample of fluid to determine a sample value of the fluid parameter for the sample; and
at least one processor configured to:
determine an overall representative value of the fluid parameter across the event period based at least in part on the sample value for the sample, and a sample in-line value corresponding to the time of extracting the sample,
wherein the sample in-line value corresponding to the time of extracting the sample is a weighted average of the in-line values at the time of the one or more rinses and the sample, wherein later obtained in-line values are given a higher weighting.

2. The system of claim 1, wherein the sample sensor is configured to perform at least two rinses of the sensing device prior to extraction of the sample.

3. The system of claim 1, wherein the extraction of the sample is performed on at least one condition being met during the event period.

4. The system of claim 3, wherein the extraction of the sample is performed by about the mid-point of an expected event period.

5. The system of claim 1, wherein the at least one processor is configured to:
determine a representative in-line value of the fluid parameter across the event period based at least in part on the at least one in-line value,
wherein the determination of the overall representative value of the fluid parameter is further based on the representative in-line value.

6. The system of claim 1, wherein the determination of the overall representative value is based on an error correction value determined for the in-line sensor during the event period.

7. The system of claim 1, wherein the determination of the overall representative value of the fluid parameter comprises:
   determining a difference between the in-line value of the fluid parameter corresponding to the time of extracting the sample, and the sample value of the fluid parameter; and
   adjusting the representative in-line value of the fluid parameter across the event period by the determined difference.

8. The system of claim 7, wherein the difference is one of: an absolute difference, and a relative difference.

9. The system of claim 1, wherein the determination of the overall representative value of the fluid parameter comprises:
   determining a difference between the in-line value of the fluid parameter corresponding to the time of extracting the sample, and the representative in-line value of the fluid parameter across the event period; and
   adjusting the sample value of the fluid parameter by the determined difference.

10. The system of claim 9, wherein the difference is one of: an absolute difference, and a relative difference.

11. The system of claim 1, wherein the fluid being analyzed is milk.

12. The system of claim 11, wherein the fluid parameter to be analyzed is fat content.

13. The system of claim 1, wherein the in-line sensor is an electromagnetic radiation-based sensor.

14. The system of claim 1, wherein the sample sensor is configured to analyze the sample of fluid using an ultrasound measurement technique.

15. A method for analyzing a fluid, comprising the steps of:
   analyzing a fluid flowing past an in-line sensor to determine at least one in-line value of a fluid parameter of the fluid across an event period;
   performing one or more rinses of a sensing device of a sample sensor with fluid extracted from the flow of fluid;
   analyzing, with the sample sensor, a sample of fluid extracted from the flow of fluid during the event period subsequent to the one or more rinses, to determine a sample value of the fluid parameter for the sample;
   determining an overall representative value of the fluid parameter based at least in part on the sample value for the sample, and a sample in-line value corresponding to the time of extracting the sample,
   wherein the sample in-line value corresponding to the time of extracting the sample is a weighted average of the in-line values at the time of the one or more rinses and the sample, wherein later obtained in-line values are given a higher weighting.

16. The method of claim 15, wherein at least two rinses of the sensing device are performed prior to extraction of the sample.

17. The method of claim 15, wherein the fluid being analyzed is milk.

18. The method of claim 17, wherein the fluid parameter to be analyzed is fat content.

19. The method of claim 15, wherein the in-line sensor is an electromagnetic radiation-based sensor.

20. The method of claim 15, wherein the sample sensor is configured to analyze the sample of fluid using an ultrasound measurement technique.

* * * * *